(12) United States Patent
Silverman

(10) Patent No.: US 6,585,751 B1
(45) Date of Patent: Jul. 1, 2003

(54) PRIVATE TANNING ENCLOSURE

(76) Inventor: Elyse Silverman, 26 Raynor Rd., Morristown, NJ (US) 07960

( * ) Notice: Subject to any disclaimer, the term of this patent is extended or adjusted under 35 U.S.C. 154(b) by 5 days.

(21) Appl. No.: 09/931,799

(22) Filed: Aug. 17, 2001

(51) Int. Cl.[7] ............................................. A61N 5/06
(52) U.S. Cl. .................................... 607/95; 607/88
(58) Field of Search .................................. 607/88, 95

(56) References Cited

U.S. PATENT DOCUMENTS

| | | |
|---|---|---|
| D208,383 S | 8/1967 | Tecton |
| 3,670,750 A | 6/1972 | Johnston |
| 4,067,347 A | 1/1978 | Lipinski |
| 4,205,684 A * | 6/1980 | Lassy .......................... 607/95 |
| 4,469,102 A * | 9/1984 | Fish ............................ 607/91 |
| 4,508,120 A * | 4/1985 | Hammond .................... 607/94 |
| 4,582,062 A * | 4/1986 | Albini ......................... 607/95 |
| 4,984,571 A * | 1/1991 | Springer et al. ............. 359/361 |
| 4,989,600 A * | 2/1991 | Collier ........................ 359/350 |
| 5,066,082 A * | 11/1991 | Longstaff .................... 428/135 |
| 5,085,212 A | 2/1992 | Decosta |
| 5,446,580 A | 8/1995 | Collins |
| 5,518,798 A * | 5/1996 | Riedel ......................... 607/91 |
| 5,733,314 A * | 3/1998 | Perrino ........................ 607/91 |
| 5,837,000 A | 11/1998 | Boudreau |

* cited by examiner

*Primary Examiner*—Lee Cohen
*Assistant Examiner*—Henry M. Johnson, III

(57) ABSTRACT

A private tanning enclosure for permitting a user to tan in privacy. The private tanning enclosure includes a collapsible frame enclosed by a porous material designed for permitting ultraviolet light in for tanning purposes, but does not allow the user inside to be seen.

8 Claims, 2 Drawing Sheets

PRIVATE TANNING ENCLOSURE

BACKGROUND OF THE INVENTION

1. Field of the Invention

The present invention relates to private tanning enclosures and more particularly pertains to a new private tanning enclosure for permitting a user to tan in privacy.

2. Description of the Prior Art

The use of private tanning enclosures is known in the prior art. More specifically, private tanning enclosures heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,670,750; U.S. Pat. No. 5,446,580; U.S. Pat. No. 5,837,000; U.S. Pat. No. 5,085,212; U.S. Pat. No. 4,067,347; and U.S. Pat. No. Des. 208,383.

While these devices fulfill their respective, particular objectives and requirements, the aforementioned patents do not disclose a new private tanning enclosure. The inventive device, includes a collapsible frame enclosed by a porous material designed for permitting ultraviolet light in for tanning purposes, but does not allow the user inside to be seen.

In these respects, the private tanning enclosure according to the present invention substantially departs from the conventional concepts and designs of the prior art, and in so doing provides an apparatus primarily developed for the purpose of permitting a user to tan in privacy.

SUMMARY OF THE INVENTION

In view of the foregoing disadvantages inherent in the known types of private tanning enclosures now present in the prior art, the present invention provides a new private tanning enclosure construction wherein the same can be utilized for permitting a user to tan in privacy.

The general purpose of the present invention, which will be described subsequently in greater detail, is to provide a new private tanning enclosure apparatus and method which has many of the advantages of the private tanning enclosures mentioned heretofore and many novel features that result in a new private tanning enclosure which is not anticipated, rendered obvious, suggested, or even implied by any of the prior art private tanning enclosures, either alone or in any combination thereof.

To attain this, the present invention generally comprises a collapsible frame enclosed by a porous material designed for permitting ultraviolet light in for tanning purposes, but does not allow the user inside to be seen.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is, it intended to be limiting as to the scope of the invention in any way.

It is therefore an object of the present invention to provide a new private tanning enclosure apparatus and method which has many of the advantages of the private tanning enclosures mentioned heretofore and many novel features that result in a new private tanning enclosure which is not anticipated, rendered obvious, suggested, or even implied by any of the prior art private tanning enclosures, either alone or in any combination thereof.

It is another object of the present invention to provide a new private tanning enclosure, which may be easily and efficiently manufactured and marketed.

It is a further object of the present invention to provide a new private tanning enclosure, which is of a durable and reliable construction.

An even further object of the present invention is to provide a new private tanning enclosure which is susceptible of a low cost of manufacture with regard to both materials and labor, and which accordingly is then susceptible of low prices of sale to the consuming public, thereby making such private tanning enclosure economically available to the buying public.

Still yet another object of the present invention is to provide a new private tanning enclosure which provides in the apparatuses and methods of the prior art some of the advantages thereof, while simultaneously overcoming some of the disadvantages normally associated therewith.

Still another object of the present invention is to provide a new private tanning enclosure for permitting a user to tan in privacy.

Yet another object of the present invention is to provide a new private tanning enclosure which includes a collapsible frame enclosed by a porous material designed for permitting ultraviolet light in for tanning purposes, but-does not allow the user inside to be seen.

Still yet another object of the present invention is to provide a new private tanning enclosure that would allow a user to tan in complete privacy wherever they wanted to.

Even still another object of the present invention is to provide a new private tanning enclosure that is collapsible, thus making it compact and portable.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
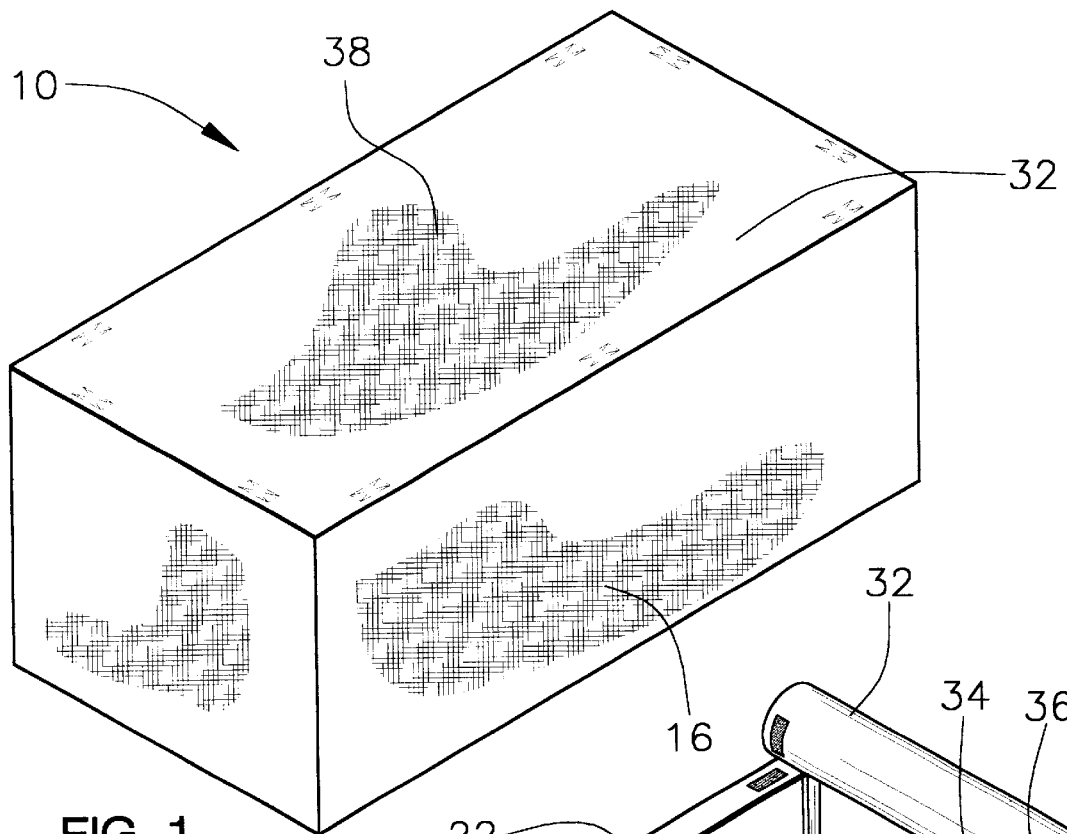
FIG. 1 is a perspective view of a new private tanning enclosure in the fully closed position.
Figure 2:
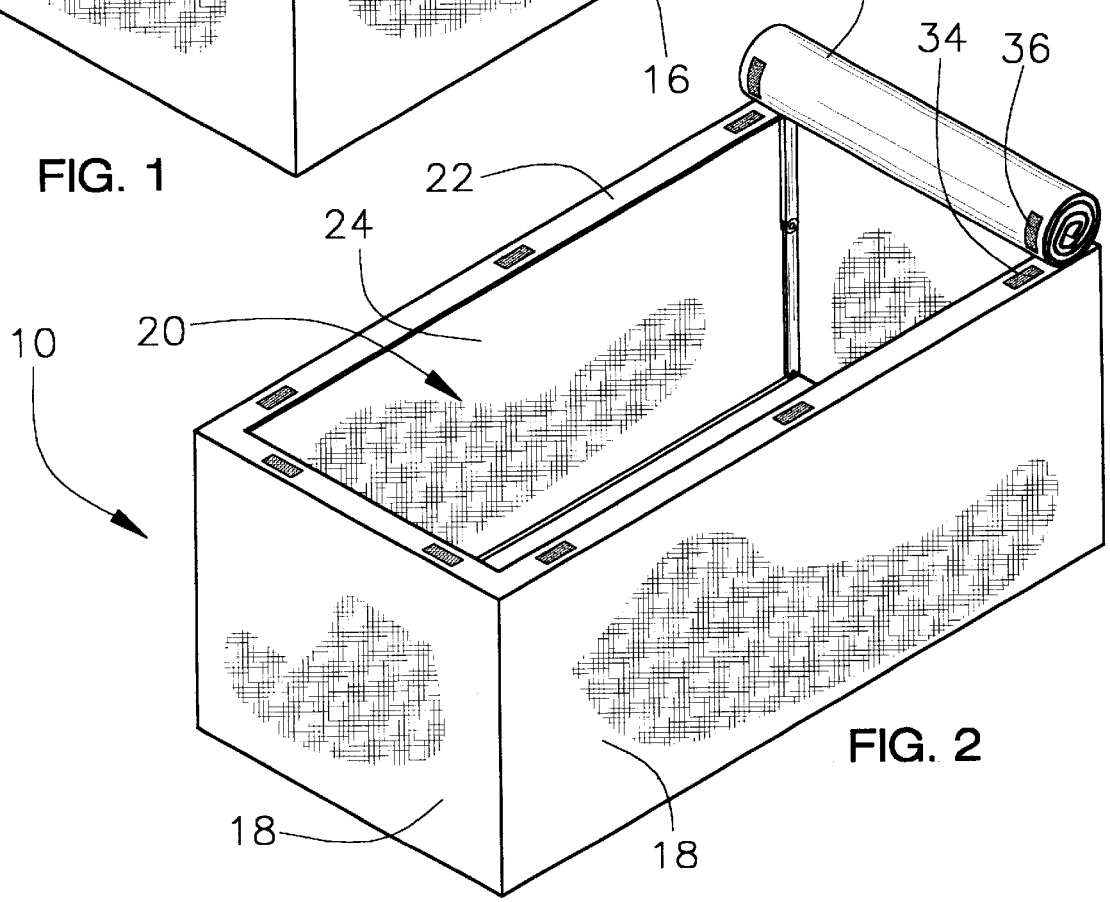
FIG. 2 is a perspective view of the present invention with the top wall in the open position.
Figure 3:
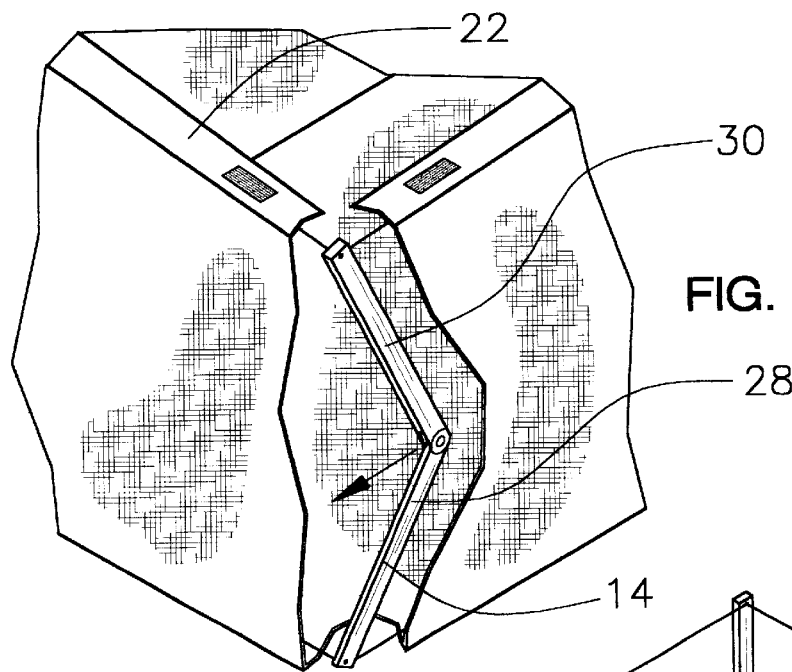
FIG. 3 is a sectional view of a collapsible leg of the present invention.
Figure 4:
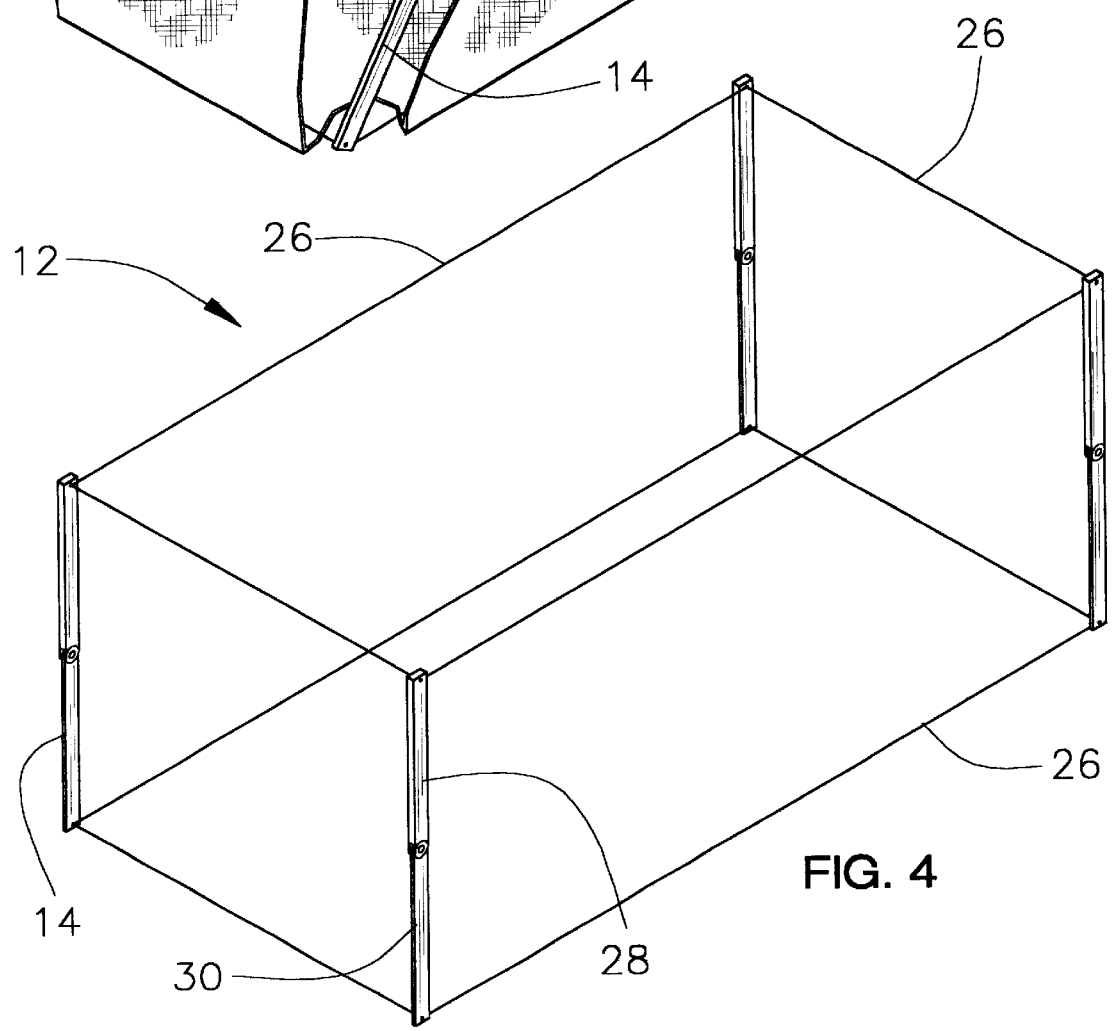
FIG. 4 is a perspective view of the frame and guide wires of the present invention.

With reference now to the drawings, and in particular to FIGS. 1 through 4 thereof, a new private tanning enclosure embodying the principles and concepts of the present invention and generally designated by the reference numeral 10 will be described.

As best illustrated in FIGS. 1 through 4, the private tanning enclosure 10 generally comprises a frame 12 that has a plurality of legs 14. The legs 14 are designed for engaging a support surface such that the frame 12 is held upright by the legs 14.

A screen member 16 that has a perimeter wall 18 coupled to the frame 12. The perimeter wall 18 defines an interior space 20 of the screen member 16 when the perimeter wall 18 is coupled to the frame 12.

The perimeter wall 18 has a top wall 22, which has an aperture 24. The aperture 24 permits access to the interior space 20 by the user when the user desires privacy. The aperture 24 is designed for permitting light to pass through to the user when the user is positioned in the interior space 20.

The frame 12 has a plurality of guide wires 26. Each of the guide wires 26 is coupled between a pair of adjacent legs 14. Each of the guide wires 26 is for maintaining the perimeter wall 18 of the screen member 16 in an erected position when the user is positioned within the interior space 20 of the screen member 16.

Each of the guide wires 26 comprises a flexible material. The flexible material of the guide wires 26 facilitates collapsing of the screen member 16 and the frame 12 for more compact storage.

Each of the legs 14 has a first portion 28 and a second portion 30. The first portion 28 of each of the legs 14 are hingably coupled to the second portion 30 of an associated one of the legs 14 such that each of the legs 14 is foldable into a compact position for facilitating storage of the frame 12 and the screen member 16.

A cover member 32 is selectively couplable to the top wall 22 of the perimeter wall 18. The cover member 32 is for selectively closing the aperture 24 through the top wall 22 when the user is positioned within the interior space 20 of the screen member 16.

The top wall 22 has a plurality of first portions of hook and loop fasteners 34. The cover member 32 has a plurality of second portions of hook and loop fasteners 36. Each of the first portions of hook and loop fasteners 34 of the top wall 22 is selectively couplable to one of the second portions of hook and loop fasteners 36 of the cover member 32 for selectively securing the cover member 32 to the top wall 22 of the perimeter wall 18 of the screen member 16.

The screen member 16 and the cover member 32 comprise a substantially porous material 38. The porous material 38 is designed for permitting ultraviolet light to pass through the screen member 16 and the cover member 32 for facilitating tanning of the user when the user is within the interior space 20 of the screen member 16.

The porous material 38 inhibits viewing of the user when the user is within the interior space 20 of the screen member 16.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A privacy tanning enclosure for permitting a user to tan in privacy, the privacy tanning enclosure comprising:
   a frame having a plurality of legs, said legs being adapted for standing on a support surface;
   a screen member having a perimeter wall, said perimeter wall being coupled to said frame, said perimeter wall defining an interior space of said screen member when corners of said perimeter wall are supported on said legs of said frame, said perimeter wall having a top wall having an aperture, said aperture being adapted for permitting access to said interior space by the user when the user desires privacy, said aperture being adapted for permitting light to pass through to the user when the user is positioned in said interior space formed by said perimeter wall of said screen member; and
   said frame having a plurality of guide wires, each of said guide wires being coupled between a pair of adjacent legs, each of said guide wires being for maintaining said perimeter wall of said screen member in an erected position when the user is positioned within said interior space formed by said interior space of said screen member.

2. The privacy tanning enclosure as set forth in claim 1, further comprising:
   each of said guide wires comprising a flexible material, said flexible material of said guide wires facilitating collapsing of said screen member and said frame for more compact storage.

3. The privacy tanning enclosure as set forth in claim 1, further comprising:

each of said legs having a first portion and a second portion, said first portion of each of said legs being hingably coupled to said second portion of an associated one of said legs such that each of said legs is foldable into a into a compact position for facilitating storage of said frame and said screen member.

4. The privacy tanning enclosure as set forth in claim 1, further comprising:

a cover member selectively couplable to said top wall of said perimeter wall, said cover member being for selectively closing said aperture through said top wall when the user is positioned within said interior space formed by said perimeter wall of said screen member.

5. The privacy tanning enclosure as set forth in claim 4, further comprising:

said top wall of said perimeter wall having a plurality of first portions of hook and loop fastener, said cover member having a plurality of second portions of hook and loop fastener, each of said first portions of hook and loop fastener of said top wall being selectively couplable to one of said second portions of hook and loop fastener of said cover member for selectively securing said cover member to said top wall of said perimeter wall of said screen member.

6. The privacy tanning enclosure as set forth in claim 4, further comprising:

said screen member and said cover member comprising a substantially porous material, said substantially porous material being adapted for permitting ultra violet light to pass through said screen member and said cover member for facilitating tanning of the user when the user is within said interior space formed by said perimeter wall of said screen member, said substantially porous material being adapted for inhibiting viewing of the user when the user is within said interior space formed by said perimeter wall of said screen member.

7. The privacy tanning enclosure as set forth in claim 1, further comprising:

said screen member comprising a substantially porous material, said substantially porous material being adapted for permitting ultra violet light to pass through said screen member for facilitating tanning of the user when the user is within said interior space formed by said perimeter wall of said screen member, said substantially porous material being adapted for inhibiting viewing of the user when the user is within said interior space formed by said perimeter wall of said screen member.

8. A privacy tanning enclosure for permitting a user to tan in privacy, the privacy tanning enclosure comprising:

a frame having a plurality of legs, said legs being adapted for standing on a support surface;

a screen member having a perimeter wall, said perimeter wall being coupled to said frame, said perimeter wall defining an interior space of said screen member when corners of said perimeter wall are supported on said legs of said frame, said perimeter wall having a top wall having an aperture, said aperture being adapted for permitting access to said interior space by the user when the user desires privacy, said aperture being adapted for permitting light to pass through to the user when the user is positioned in said interior space formed by said perimeter wall of said screen member;

said frame having a plurality of guide wires, each of said guide wires being coupled between a pair of adjacent legs, each of said guide wires being for maintaining said perimeter wall of said screen member in an erected position when the user is positioned within said interior space formed by said interior space of said screen member;

each of said guide wires comprising a flexible material, said flexible material of said guide-wires facilitating collapsing of said screen member and said frame for more compact storage;

each of said legs having a first portion and a second portion, said first portion of each of said legs being hingably coupled to said second portion of an associated one of said legs such that each of said legs is foldable into a into a compact position for facilitating storage of said frame and said screen member;

a cover member selectively couplable to said top wall of said perimeter wall, said cover member being for selectively closing said aperture through said top wall when the user is positioned within said interior space formed by said perimeter wall of said screen member;

said top wall of said perimeter wall having a plurality of first portions of hook and loop fastener, said cover member having a plurality of second portions of hook and loop fastener, each of said first portions of hook and loop fastener of said top wall being selectively couplable to one of said second portions of hook and loop fastener of said cover member for selectively securing said cover member to said top wall of said perimeter wall of said screen member;

said screen member and said cover member comprising a substantially porous material, said substantially porous material being adapted for permitting ultra violet light to pass through said screen member and said cover member for facilitating tanning of the user when the user is within said interior space formed by said perimeter wall of said screen member, said substantially porous material being adapted for inhibiting viewing of the user when the user is within said interior space formed by said perimeter wall of said screen member.

* * * * *